(12) United States Patent
Hutzenlaub et al.

(10) Patent No.: US 8,927,257 B2
(45) Date of Patent: Jan. 6, 2015

(54) ORGAN TRANSPORT CONTAINER SYSTEM

(75) Inventors: Jens Peter Hutzenlaub, Aachen (DE); Timm Michael Schroeder, Aachen (DE); Arjan Van Der Plaats, Winschoten (NL); Gerhard Rakhorst, Groningen (NL)

(73) Assignee: Organ Assist B.V., Groningen (NL)

( * ) Notice: Subject to any disclaimer, the term of this patent is extended or adjusted under 35 U.S.C. 154(b) by 811 days.

(21) Appl. No.: 12/680,437

(22) PCT Filed: Sep. 28, 2007

(86) PCT No.: PCT/NL2007/050474
§ 371 (c)(1),
(2), (4) Date: Jul. 27, 2010

(87) PCT Pub. No.: WO2009/041806
PCT Pub. Date: Apr. 2, 2009

(65) Prior Publication Data
US 2011/0033916 A1 Feb. 10, 2011

(51) Int. Cl.
*A01N 1/00* (2006.01)
*A01N 1/02* (2006.01)
*C12M 3/00* (2006.01)

(52) U.S. Cl.
CPC .............. *A01N 1/02* (2013.01); *C12M 21/08* (2013.01); *A01N 1/0247* (2013.01); *A01N 1/0273* (2013.01)
USPC ........ 435/284.1; 435/1.1; 435/1.2; 435/289.1

(58) Field of Classification Search
CPC ..... A01N 1/02; A01N 1/0247; A01N 1/0273; C12M 21/08

USPC .............................. 435/1.1, 1.2, 284.1, 289.1
See application file for complete search history.

(56) References Cited

U.S. PATENT DOCUMENTS

| 5,586,438 | A | * | 12/1996 | Fahy .................................. 62/78 |
| 5,985,653 | A | | 11/1999 | Armstrong et al. |
| 6,046,046 | A | | 4/2000 | Hassanein |
| 7,176,015 | B2 | | 2/2007 | Alford et al. |

(Continued)

FOREIGN PATENT DOCUMENTS

| FR | 2 513 884 A1 | 4/1983 |
| GB | 2110564 A | 6/1983 |

(Continued)

*Primary Examiner* — Nathan Bowers
(74) *Attorney, Agent, or Firm* — Pearne & Gordon LLP

(57) ABSTRACT

An organ transport container system for storing and transporting therein an organ coupled to a perfusion system for preserving the viability of the organ for implantation by perfusing the organ with a perfusion liquid. The container system includes a cartridge for carrying the organ and a receptacle for holding a volume of the perfusion liquid and for removably holding therein the cartridge in a transport position. The cartridge has a holder for supporting the organ and relay conduit extending between an artery connector for sealingly connecting the relay conduit to an artery of the organ in the holder and an inlet. An outlet of a passage through the receptacle wall or bottom and the inlet are positioned and arranged such that the outlet and the inlet are sealingly coupled to each other when the cartridge is brought in the transport position, for allowing preservation liquid supplied via the supply conduit to be relayed to the artery via the relay conduit when the cartridge is in the transport position.

12 Claims, 6 Drawing Sheets

(56) References Cited

U.S. PATENT DOCUMENTS

| | | | |
|---|---|---|---|
| 7,572,622 B2 * | 8/2009 | Hassanein et al. | 435/284.1 |
| 2004/0171138 A1 | 9/2004 | Hassanein et al. | |
| 2004/0235142 A1 * | 11/2004 | Schein et al. | 435/284.1 |
| 2005/0147538 A1 * | 7/2005 | Williamson et al. | 422/102 |
| 2005/0186671 A1 * | 8/2005 | Cannon et al. | 435/297.2 |
| 2006/0141623 A1 * | 6/2006 | Smith et al. | 435/383 |
| 2009/0298043 A1 | 12/2009 | Mangino | |
| 2011/0300614 A1 * | 12/2011 | Owen et al. | 435/284.1 |

FOREIGN PATENT DOCUMENTS

| | | |
|---|---|---|
| WO | 2004/089235 A2 | 10/2004 |
| WO | 2005009125 A1 | 2/2005 |
| WO | 2007082203 A2 | 7/2007 |

* cited by examiner

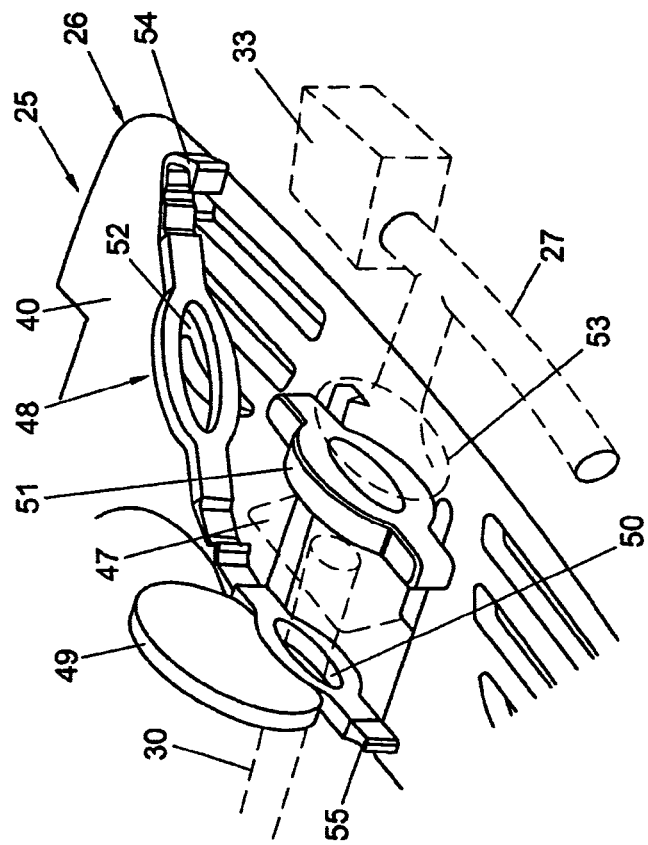
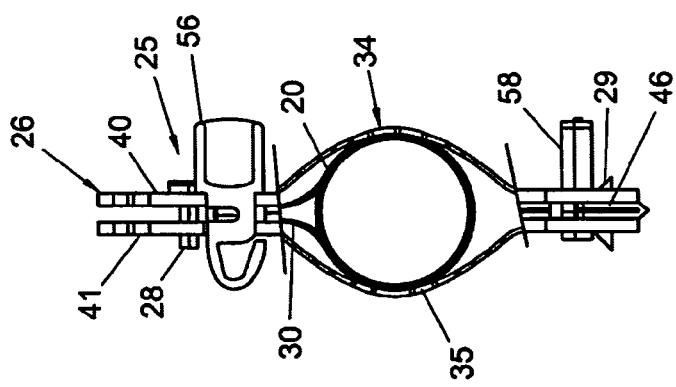
FIG. 4
FIG. 3

ORGAN TRANSPORT CONTAINER SYSTEM

FIELD AND BACKGROUND OF THE INVENTION

The invention relates to an organ transport container system for storing and transporting therein an organ coupled to an apparatus for preserving the viability of the organ for implantation by perfusing the organ with a perfusion liquid.

The transplantation procedure of an organ involves three stages, 1) the donor operation, 2) the preservation and transportation of the organ and 3) the implantation in the recipient.

In the common preservation procedure, known as "static cold storage" (CS), after the initial wash out with preservation liquid, the organ is packed in a bag filled with preservation liquid, which in turn is placed in a bag with cold physiological salt, which in turn is placed in a third bag for sturdiness and is finally stored in a cooling box with melting ice.

A drawback, of this procedure is the possibility of organ decay due to e.g. a lack of perfusion that enables the delivery of oxygen, an unusual position of the organ, or possible problems with sterility.

In international patent application WO2005/009125, a portable preservation apparatus is described that allows continuous perfusion of an organ and includes a pulsating pump system integrated in a cooling box with a cold oxygenated preservation liquid (4° C.), which provides besides delivery of oxygen to the organ also a means for cooling the organ. An organ chamber intended to cooperate with such a device has to meet extra demands concerning structure and connections, while still complying with requirements of sterile handling and ease-of-use. The organ is transported in a bag filled with preservation liquid in which the organ has been placed immediately after explantation from the deceased donor body and canulas are connected to the organ. This involves manipulations with the organ, which are time consuming and therefore increase the risk of damage to the organ due to delayed cooling and oxygen supply. Also the risk of mechanical damage to the organ increases with the amount of manipulations to which the organ is subjected.

In international patent application WO2004/089235, an apparatus for transport and storage of an organ is described, which includes a cassette for carrying the organ and a receptacle for holding a volume of the perfusion liquid and for removably holding therein the cartridge in a transport position. The cartridge has an organ supporting surface of porous, perforated or mesh material on which the organ may be arranged. The cassette carrying the organ is positioned in an organ chamber of the receptacle. The cassette may be provided with tubing for connection to an organ and/or to remove medical liquid from the organ bath, and a connection device(s) for connecting the tubing to, for example, tubing of the organ storage, transporter, perfusion and/or diagnostic apparatus. Positioning the organ in the apparatus is facilitated, but still requires extensive manipulations for connecting canulas to the preservation liquid supply, before the transport may started. With the time required for the manipulations, the risk of warm ischemia and contamination of the organ increases. Also, the organ is supported in an unusual manner, which increases the risk of causing damage to the organ.

SUMMARY OF THE INVENTION

It is an object of the present invention to provide a solution which allows to store the organ more quickly and easily in an apparatus for perfusing the organ during transport and storage. According to the present invention, this object is achieved by providing an organ transport container system for storing and transporting therein an organ coupled to a perfusion system for preserving the viability of the organ for implantation by perfusing the organ with a perfusion liquid, the container system comprising a cartridge for carrying the organ and a receptacle for holding a volume of the perfusion liquid and for removably holding therein the cartridge in a transport position, the cartridge comprising:

a holder for supporting the organ immersed in the perfusion liquid in the receptacle if the cartridge is in the transport position in the receptacle; and a relay conduit extending between an artery connector for sealingly connecting the relay conduit to an artery of the organ in the holder and an inlet; and the receptacle comprising an outlet for forming a downstream end of a preservation liquid supply conduit, wherein the outlet and the inlet are positioned and arranged such that the outlet and the inlet are sealingly coupled to each other when the cartridge reaches the transport position in the receptacle, for allowing preservation liquid supplied via the supply conduit to be relayed to the artery via the relay conduit when the cartridge is in the transport position.

Because the outlet and the inlet are positioned and arranged such that the outlet and the inlet are sealingly coupled to each other when the cartridge is brought in the transport position, for allowing preservation liquid supplied via the supply conduit to be relayed to the artery of the organ via the relay conduit when the cartridge is in the transport position, a coupling between the supply conduit and the relay conduit is automatically established when the cartridge is inserted into the receptacle and reaches its transport position. Thus the amount of manipulation and accordingly the risk of contamination of the organ and the risk of damage to the organ is substantially reduced.

Further features, effects and details of the invention appear from the detailed description and the drawings.

BRIEF DESCRIPTION OF THE DRAWINGS

FIG. 3 is a partially cut-away view of the cartridge shown in FIG. 2 in closed condition and carrying an organ;

FIG. 4 is a perspective view of a portion of the cartridge shown in FIGS. 2 and 3 with a connector for connecting a relay conduit to an artery connected to an organ;

DETAILED DESCRIPTION OF PREFERRED EMBODIMENTS

Figure 1:
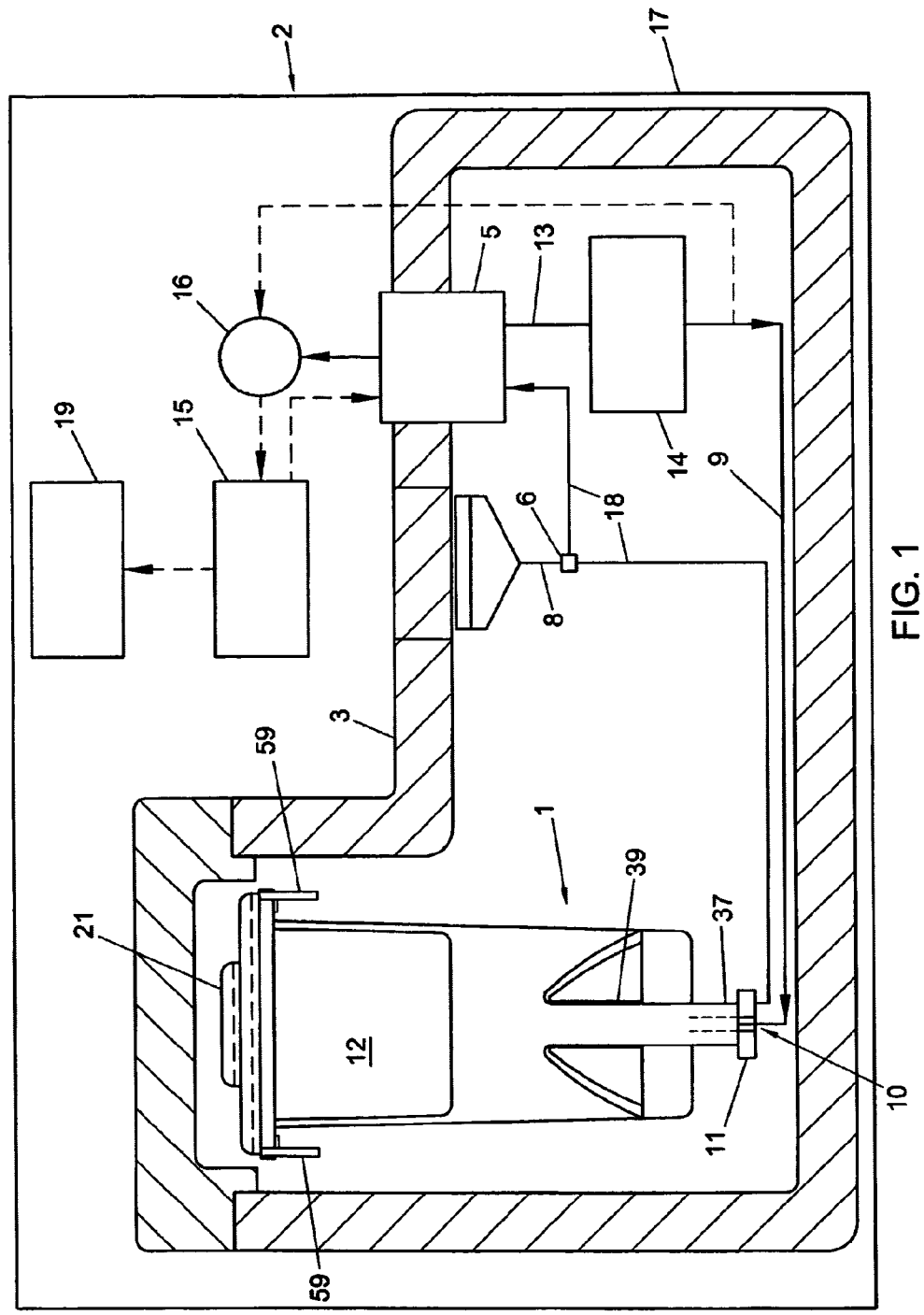
FIG. 1 is a partially diagrammatic representation of an organ perfusion apparatus including an example of an organ transport container system according to the invention.

In FIG. 1, an example of an organ transport container system 1 according to the invention is shown as part of an example of a portable organ preservation apparatus 2. For features of the portable organ preservation apparatus other than the container system 1, reference is made to commonly assigned international patent application WO2005/009125, the contents of which is hereby incorporated by reference.

The container system 1 is arranged in a thermal insulation 3 and, when in use, contains an organ to be implanted in a patient. In the present example, the organ is a kidney. However, also other organs may be transported and may require adaptations of the apparatus to accommodate to differences in shape, dimensions and morphology between organs. During the procurement of a kidney, normally the renal artery and a flange cut taken from the aorta where the renal artery diverges from the aorta are left connected to the kidney. To this renal artery, a supply conduit 9 is connected, of which a section 10 extends through a receptacle connector 11. The supply conduit is connected to an oxygenator 14 and the oxygenator 14 is connected to a pump 5 via a conduit 13. The renal vein ends in a chamber in a receptacle 12 of the container system 1, in which chamber also the kidney is stored. The pump 5 is connected to the chamber inside the receptacle 12 via a recirculation conduit 18 for pumping liquid out of the chamber so that the liquid can be recirculated. The thermal insulation 3 also encloses the other parts of the portable organ preservation apparatus 2 through which perfusion liquid flows when the apparatus is in use.

The pump 5 is preferably designed such that, selectively, either a continuous working mode or a pulsatile working mode is possible, so that, physiologically optimal perfusion conditions can be achieved. The connections may be adapted for a different organ depending on the specific organ. For a liver, for instance, two connections for supplying perfusion liquid to the organ would be preferred.

A control device 15 is provided for controlling the pump 5 in response to the pressure P detected by pressure sensor 16 downstream of the oxygenator 14. The control device 15 is also connected to control unit 19 provided with a user interface (not shown), for instance in the form of a touch screen display, which is arranged to display relevant information, such as pressure in the canulas, flow velocity and/or flow rate, temperature, time, alarm condition etc.

For filling the receptacle with perfusion liquid, a filling connector 6 is provided communicating with the supply conduit 9 for filling perfusion liquid into the receptacle 12. A bag 7 or other container containing perfusion liquid may be connected to the filling connector 6, for instance via a canule 8. Because the filling connector 6 is located upstream of the pump 5, activating the pump 5 causes the perfusion liquid to be transferred from the container 7 to the chamber inside the receptacle 12. The transfer of the perfusion liquid may also be driven by gravity. Prior to bringing the organ into the receptacle 12, liquid may be oxygenated, and cooled if a cooler is also provided, by activating the pump 5, and optionally the cooler, after the perfusion liquid has been transferred to the chamber in the receptacle 12, so that perfusion liquid is circulated through the chamber in the receptacle 12, the recirculation conduits 18, the pump 5, the conduit 13, the oxygenator 14 and the supply conduit 9. Such recirculation prior to bringing the organ into the receptacle also provides the advantage of driving air out of the system.

Preferably, the container system 1, a pumping head of the pump 5, the bag 7 with tubing 8, the oxygenator 14 and the pressure sensor 16, which come into contact with perfusion liquid when in use, are provided in the form of single use items, whereas at least the thermal insulation 3, a drive part of the pump 5, the control device 15, the control unit 19 and a housing 17, which do not contact the perfusion liquid when in use, are provided in reusable form.

Figure 6:
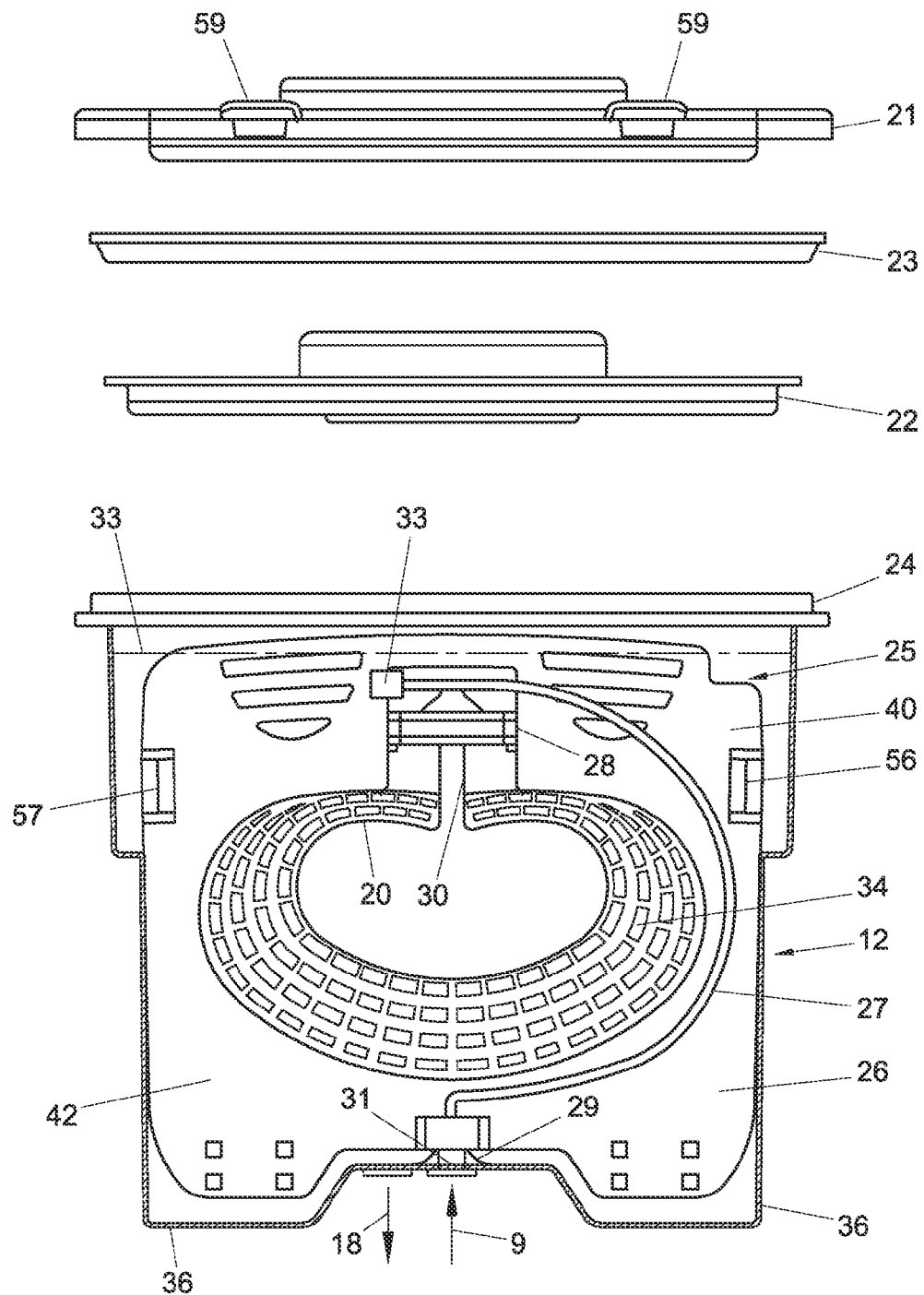
FIG. 6 is a side view of the cartridge shown in FIGS. 2-5 and the receptacle shown in FIG. 5 seen in cross-section along a mid-plane in combination with a side view of lids.
Figure 7:
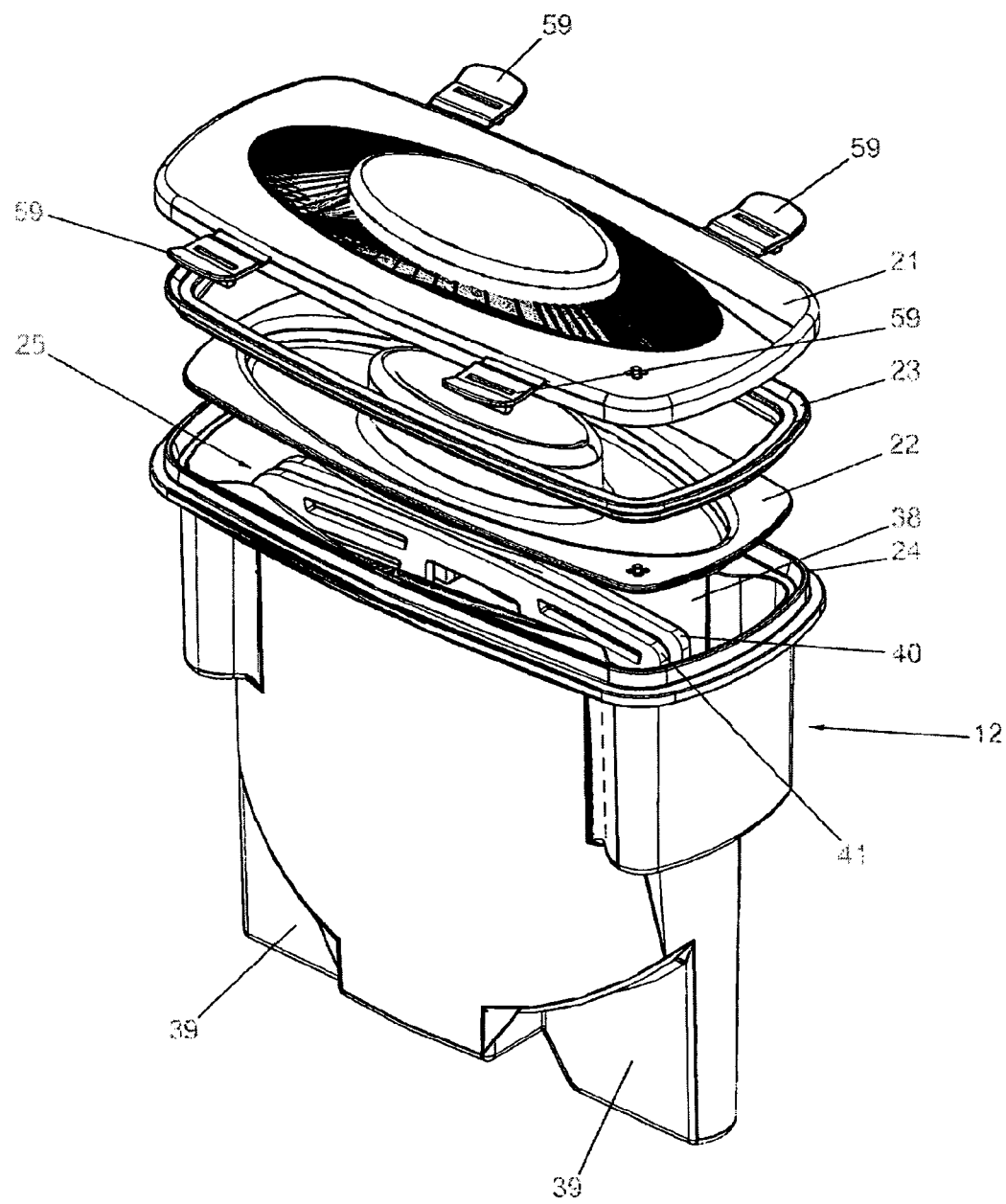
FIG. 7 is a perspective view of the container system in the condition shown in FIG. 6.

The organ transport container system is shown in more detail in a condition containing a kidney 20 and with an outer lid 21, an inner lid 22 and a sealing member 23 lifted from an upper end portion 24 of the receptacle in FIGS. 6 and 7.

The container system 1 is composed of a cartridge 25 for carrying the organ 20 and the receptacle 12 for holding a volume of the perfusion liquid and for removably holding therein the cartridge 25. In FIGS. 6 and 7, the cartridge 25 is shown in a transport position.

The cartridge 25 is equipped with a holder 26 for supporting the kidney 20 and a relay conduit 27 extending between an artery connector 28 for sealingly connecting the relay conduit 27 to an artery 30 of the kidney 20 in the holder 26 and an inlet 29. In the present example, the relay conduit 27 is formed by a tube mounted to the holder 26.

The receptacle has an outlet 31 forming a downstream end of the preservation liquid supply conduit 9. In the present example, this outlet is formed by an inner end 31 of a passage through a bottom portion of the receptacle 12.

The outlet 31 and the inlet 29 are positioned and arranged such that the outlet 31 and the inlet 29 are sealingly coupled to each other when the cartridge 25 is brought in the transport position, for allowing preservation liquid supplied via the supply conduit 9 to be relayed to the artery 30 via the relay conduit 27 when the cartridge 25 is in the transport position. The inlet 29 is formed by a flange of flexible material that sealingly connects the inlet 29 of the relay conduit 27 to the outlet passage 31 in the receptacle 12 when the inlet flange 29 rests on the inner surface of the receptacle around the outlet passage 31.

Figure 5:
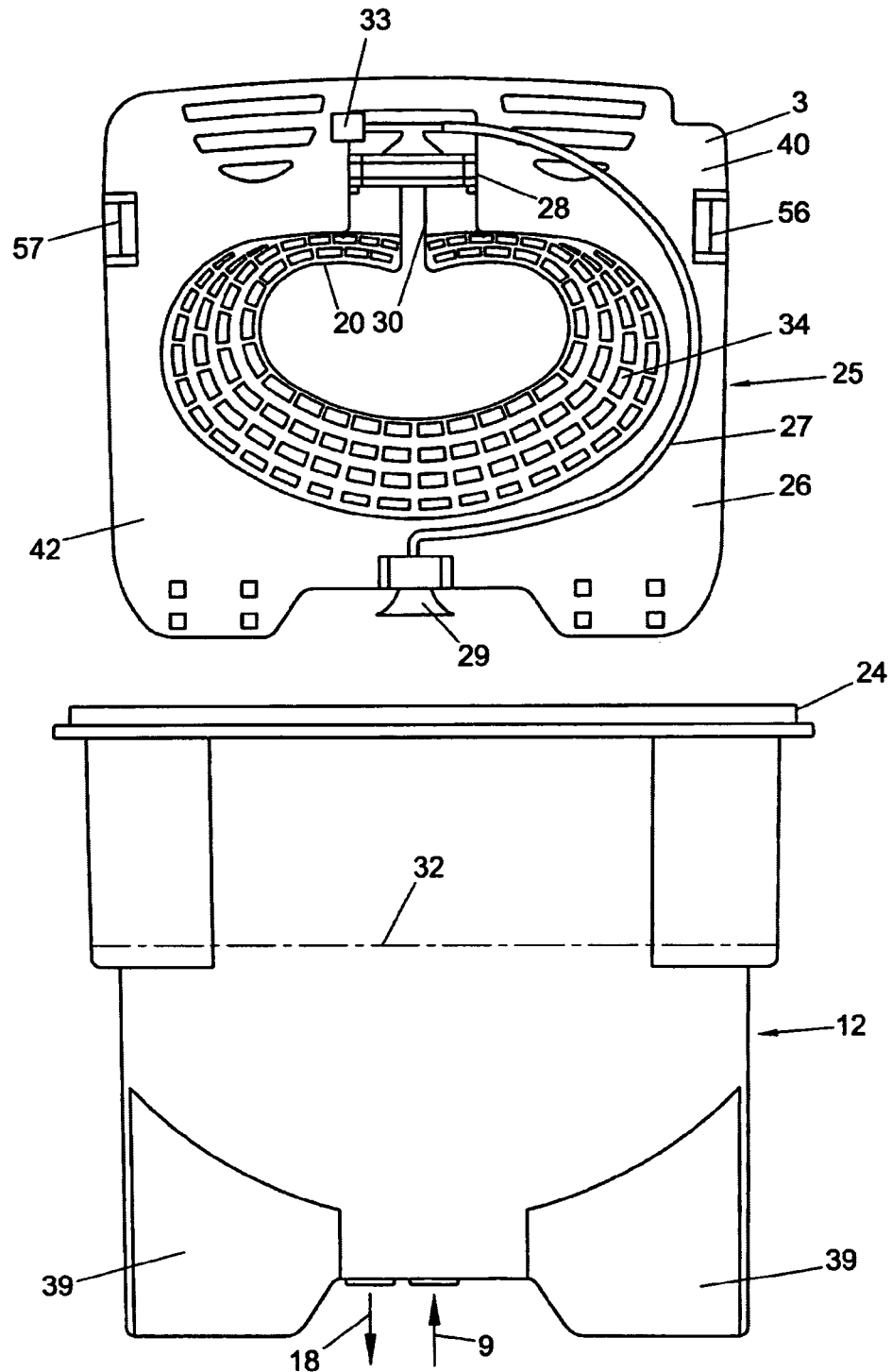
FIG. 5 is a side view of the cartridge shown in FIGS. 2-4 seen in cross-section along a mid-plane in closed condition and carrying an organ above a receptacle of the container system shown in FIG. 1.

When the cartridge 25 carrying the kidney 20 is inserted into the receptacle, for instance from the position shown in FIG. 5 to the position shown in FIGS. 6 and 7, the sealing connection of the relay conduit 27 to the supply conduit 9 is automatically established when the cartridge 25 reaches its transport position in the receptacle 12. Thus, the need of manipulations for connecting tubing connected to the kidney 20 to the supply and recirculation conduits is avoided and valuable time is saved. Furthermore, the risk of contamination of the kidney 20 is reduced, because the receptacle 12, which is supplied in a closed, sterile condition, needs to be open for receiving the kidney 20 for a very short time only.

It is observed that, instead of in a bottom wall portion of the receptacle, the outlet may also be located in a side wall portion of the receptacle if the inlet of the relay conduit is positioned accordingly for causing the inlet and the outlet to be connected to each other when the cartridge is in the transport position.

Before the cartridge 25 is lowered into the receptacle 5, the perfusion liquid level in the receptacle 12 may for instance be as is indicated by dot-and-dash line 32 in FIG. 5. After the cartridge 25 has been lowered into its transport position, the liquid displacement caused by the cartridge 25 and the kidney 20 being lowered into the perfusion liquid may for instance cause the liquid level in the receptacle 12 to reach a level indicated by dot-and-dash line 33 in FIG. 6. As can be seen from FIG. 6, the kidney 20 is then fully immersed in the perfusion liquid, which is advantageous for reducing local forces exerted thereon.

Because the inlet 29 is located below a deareating member 33 communicating with the relay conduit 27 for deareating the relay conduit 27, when the cartridge 25 is in the transport position in the receptacle 12 and the receptacle 12 is oriented upright, air in the relay conduit 27 is displaced out of the relay conduit 27 as the relay conduit is immersed in the perfusion liquid in the receptacle 12. Thus, air is reliably displaced out of the relay conduit. The deareating member 33 is preferably a deareating valve, but may also be constituted by a portion of the relay tubing or a housing communicated therewith, in which an opening is provided and that is equipped with a closure for closing off that opening, such as a plug or a manually or electrically operated valve.

The cartridge 25 has rack portions 34, 35 forming areas for holding the kidney 20 in a kidney holding area. Because the deareating member 33 is located above the kidney holding area when the cartridge 25 is in the transport position in the receptacle 12 and the receptacle 12 is oriented upright, also the artery of the kidney 30 is effectively deareated and it is effectively counteracted that any remaining bubbles are entrained to the kidney. In the container system according to the present example, the deareation of the artery 30 is particularly effective, because the artery 30 projects substantially vertically upwards from the kidney 20 when the cartridge 25 holding the kidney 20 is in its transport position in the upright receptacle 12.

The receptacle 12 has two mutually spaced cartridge positioning slots. In the present example, these slots are formed by portions 36 of the kidney storage chamber 38 that are located in wings 39 at a lower end of the receptacle. The slots 36 are shaped and dimensioned for guiding the cartridge 25 to the transport position during insertion of the cartridge 25 and for holding the cartridge 25 in the transport position. Because the receptacle is narrow in the area of the wings 39, the chamber 38 of the receptacle 12 has little volume in the area where the cartridge 25 is guided, so the amount of perfusion liquid required to immerse the kidney 20 is relatively small. Also the feature that the dimensioning and the shape of the chamber 36 match the general dimensions and shape in which virtually all kidneys fit contributes to reducing the amount of perfusion liquid required to immerse the kidney 20.

According to the present example, the holder 26 is formed by two carrier members 40, 41 coupled to each other and shaped and dimensioned for holding the kidney between the carrier members 40, 41. As is best seen in FIG. 3, the carrier members 40, 41 are deformable for accommodating their shapes to the shape of a kidney 20 held between the carrier members 40, 41. The kidney 20 is held reliably between the carrier members 40, 41 also while the cartridge 25 is placed in the receptacle 12 and taken out of the receptacle, while deformation of the kidney is, at least to a large extent, avoided. Although it is preferred that both carrier members are deformable for accommodating their shapes to the shape of a kidney held between the carrier members, it is also possible to provide that only one of the carrier members is deformable for accommodating to the shape of a kidney held between the carrier members. Also, more than two carrier members may be provided. The kidney may for instance be held between three or more carrier members enclosing the kidney from three or, respectively, more sides.

It is observed that, although particularly advantageous in a container system in which the relay conduit connects to a supply conduit when the cartridge containing the organ is positioned in the receptacle, the features that the holder comprises at least two carrier members coupled to each other and shaped and dimensioned for holding the organ between the carrier members, an that at least one of the carrier members is deformable for accommodating its shape to the shape of an organ held between the carrier members, are also advantageous for reliably holding an organ with little deformation in a container system in which the outlet and the inlet are not positioned and arranged such that the outlet and the inlet are sealingly coupled to each other when the cartridge is brought in the transport position.

The carrier member 40, 41 are each mainly composed of a generally flat frame 42, 43 and the flexible rack 34, 35 each carried by one of the frames 42, 43. The racks 34, 35 provide deformability and an even distribution of pressure exerted on the kidney 20, while leaving openings allowing perfusion liquid to pass through. The racks 34, 35 are preferably made of a more flexible material than the frames 42, 43, but the flexibility of the racks may also be achieved by the design of the pattern of holes and/or the dimensioning of the material between which the holes are left.

Figure 2:
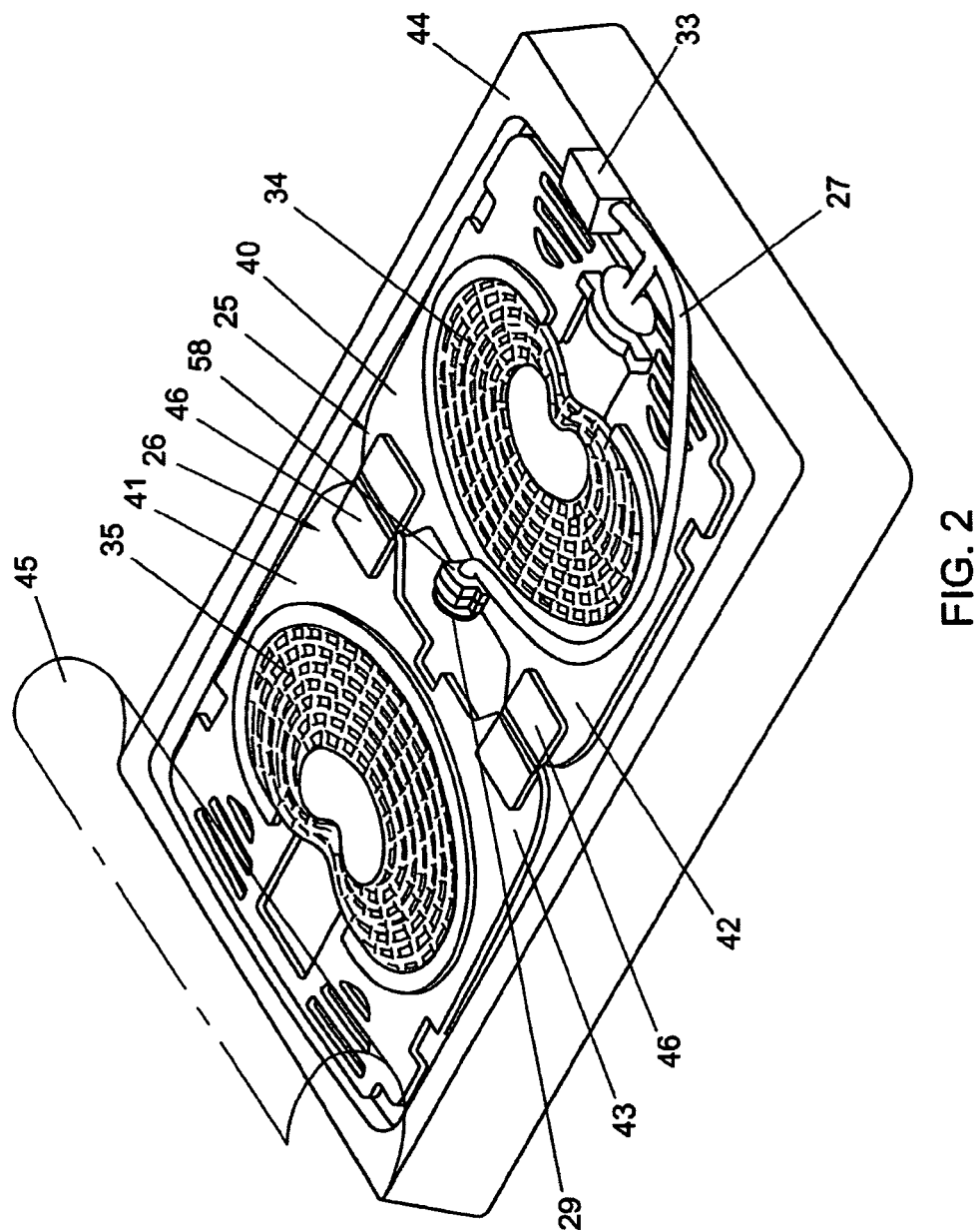
FIG. 2 is a perspective view of an example of a cartridge for carrying an organ of an organ transport container system according to the invention in a package for maintaining the cartridge sterile until the package is opened.

As is shown in FIG. 2, the container system may be provided in a package having a bottom part 44 and a cover 45 (shown partially only) containing the carrier members 40, 41. The carrier members 40, 41 are hinged to each other by means of hinge elements 46 and packaged in a generally flat configuration, hinged away from each other, with sides of the carrier members 40, 41 to be facing each other when the carrier members 40, 41 are pivoted towards each other facing away from the bottom part 44 of the package.

In use, the carrier members 40, 41 can be supplied to the location where the kidney 20 is to be explanted in sterile condition, hermetically enclosed by the bottom part 46 and the cover 45 of the package. Just before the kidney 20 is actually taken out of the donor body, the cover 45 is removed from the bottom part 44 of the package, leaving the carrier members 40, 41 uncovered. The kidney 20 is then positioned directly on the carrier member 40 to which a portion of the artery connector 28 is mounted and the artery 30 is connected to the artery connector.

As is best seen in FIG. 4, connecting the artery 30 to the artery connector 28 is achieved by guiding the free end of the artery 30 including a flange 47 of aortic wall material through a first passage 50 in a clamp 48 of the artery connector 28. The clamp 48 has a grip 49 which allows to hold the clamp 48 easily while it is mounted. The flange 47 is then pushed against a bow frame 51 of the carrier member 40 and a portion of the clamp 48 through which a second passage 52 extends is folded around the bow frame 51 and against a side of the bow frame 51 opposite the side against which the flange 47 of aortic wall material is pushed. Then a sealing flange 53 of the relay conduit 27 is passed through the second passage 52 and sealingly clamped to the bow frame 51 when the clamp 48 is closed by causing first and second hooks 54, 55 to engage.

Then, the other carrier member 41 is pivoted against the carrier member on which the kidney has been positioned and to which the artery 30 of the kidney has been connected, so that the general configuration as shown in FIG. 3 is reached.

For holding the carrier members 40, 41 together in the configuration pivoted towards each other for holding the kidney thereinbetween, closing members 56, 57 are provided. The closing members 56, 57 and a clamp 58 by means of which the inlet 29 is mounted to the frame 42 are equipped with support spacers for keeping the rack 34 against which the kidney 20 rests clear from a support surface, when the cartridge 25 containing the kidney 20 is positioned on a flat surface with the support spacers downwards.

As is illustrated by FIGS. 5 and 6, the cartridge 25 in the configuration shown in FIG. 3 can easily be inserted into the receptacle 12 which has previously been positioned in the thermal insulation 3 (with the lid thereof still open), connected to supply conduit 9 and recirculation conduit 18 and filled with perfusion liquid. As the cartridge 25 is inserted into the receptacle 12, the sealed connection between the inlet 29 of the relay conduit 27 and the outlet 31 of the supply conduit 9 is automatically established.

For hermetically closing off the receptacle 12, the inner lid 22 is arranged inside the outer edge 24 of the receptacle 12 and the outer lid 21 is brought in a position extending outside the outer edge 24 of the receptacle 12 and pressing the sealing member 23 and the inner lid 22 against the receptacle 12. Clips 59 are then closed to reliably keep the outer lid 21 clamped to the receptacle 12.

It is evident to the skilled person that many alternatives, modifications and variations may be made without departing from the spirit and scope of the invention as apparent from the claims in the light of the description.

The invention claimed is:

1. An organ transport container system for storing and transporting therein an organ coupled to a perfusion system for preserving the viability of the organ for implantation by perfusing the organ with a perfusion liquid, the container system comprising a cartridge for carrying the organ and a receptacle for holding a volume of the perfusion liquid and for removably holding the cartridge in a transport position lowered into the perfusion liquid held by the receptacle,
   the cartridge comprising:
      an inlet;
      a holder effective to support the organ immersed in the perfusion liquid held by the receptacle when the cartridge is in the transport position; and
      a relay conduit extending between (a) an artery connector for sealingly connecting the relay conduit to an artery of the organ in the holder and (b) the inlet; and
   the receptacle comprising an outlet for forming a downstream end of a preservation liquid supply conduit, the outlet defining an opening through a wall of the receptacle,
   wherein the outlet and the inlet are positioned and arranged such that the outlet and the inlet are sealingly coupled to each other automatically when the cartridge reaches the transport position, for allowing preservation liquid supplied via the supply conduit through the outlet and in through the inlet to be relayed to the artery via the relay conduit when the cartridge is in the transport position.

2. A container system according to claim 1, wherein the inlet is located below a deaerating member communicating with the relay conduit for deaerating the relay conduit, when the cartridge is in the transport position in the receptacle and the receptacle is oriented upright.

3. A container system according to claim 1, wherein the cartridge is arranged for holding the organ in an organ holding area and wherein a deaerating member is located above the organ holding area when the cartridge is in the transport position in the receptacle and the receptacle is oriented upright.

4. A container system according to claim 1, wherein the receptacle further comprising at least two mutually spaced cartridge positioning slots shaped and dimensioned for guiding the cartridge to the transport position during insertion of the cartridge and for holding the cartridge in the transport position.

5. A container system according to claim 1, wherein the holder comprises at least two carrier members coupled to each other and shaped and dimensioned for holding the organ between the carrier members, wherein at least one of the carrier members is deformable for accommodating its shape to the shape of an organ held between the carrier members.

6. A container system according to claim 5, wherein at least two of the carrier members are deformable for accommodating their shapes to the shape of the organ held thereinbetween.

7. A container system according to claim 5, wherein the at least one deformable carrier member comprises a generally flat frame and a flexible rack carried by the frame.

8. A container system according to claim 5, further comprising a package comprising a bottom part and a cover containing the carrier members, wherein the carrier members are hinged to each other and packaged in a generally flat configuration, hinged away from each other, with sides of the carrier members to be facing each other when the carrier members are pivoted towards each other facing away from the bottom part of the package.

9. A container system according to claim 5, further comprising a closing member for holding the carrier members together in a configuration pivoted towards each other for holding the organ thereinbetween.

10. A container system according to claim 1, further comprising a filling connector communicating with the supply conduit for filling perfusion liquid into the receptacle.

11. A container system according to claim 1, further comprising an inner lid located inside an outer edge of the receptacle and an outer lid extending outside the outer edge of the receptacle and pressing the inner lid against the receptacle.

12. A portable organ preservation apparatus comprising:
   at least one pump;
   an oxygenator connected to the pump for oxygenating liquid displaced by pumping action of the at least one pump;
   a supply conduit;
   a container system for storing and transporting therein an organ coupled to a perfusion system for preserving the viability of the organ for implantation by perfusing the organ with a perfusion liquid, the container system comprising a cartridge for carrying the organ and a receptacle for holding a volume of the perfusion liquid and for removably holding the cartridge in a transport position lowered into the perfusion liquid held by the receptacle;
   the cartridge comprising:
      an inlet;
      a holder effective to support the organ immersed in the perfusion liquid held by the receptacle when the cartridge is in the transport position; and
      a relay conduit extending between (a) an artery connector for sealingly connecting the relay conduit to an artery of the organ in the holder and (b) the inlet; and
   the receptacle comprising an outlet for forming a downstream end of a preservation liquid supply conduit, the outlet defining an opening through a wall of the receptacle;
   wherein the outlet and the inlet are positioned and arranged such that the outlet and the inlet are sealingly coupled to each other automatically when the cartridge reaches the transport position, for allowing preservation liquid supplied via the supply conduit through the outlet and in through the inlet to be relayed to the artery via the relay conduit when the cartridge is in the transport position;
   wherein the outlet forms a downstream end of the supply conduit; and
   wherein a recirculation conduit connects the receptacle to the pump or at least one of the pumps for pumping liquid out of the receptacle so that the liquid perfused through the organ can be recirculated.

* * * * *